United States Patent [19]

Spilman et al.

[11] 4,106,490

[45] Aug. 15, 1978

[54] URINE COLLECTION AID

[75] Inventors: Raymond Spilman; Edward Emil Haase, Jr.; Kurt John Kruger; Donald Barry Budnick; Vincent John Lasorso, Jr., all c/o Raymond Spilman Industrial Design 217 Bedford St., Stamford, Conn. 06901

[73] Assignees: Raymond Spilman; Edward Emil Haase, Jr.; Kurt John Kruger; Donald Barry Budnick; Vincent John Lasorso, Jr.; Louis H. Reens

[21] Appl. No.: 726,938

[22] Filed: Sep. 27, 1976

[51] Int. Cl.² ............................................... A61B 5/00
[52] U.S. Cl. .................................... 128/2 F; 128/295
[58] Field of Search .................... 128/2 F, 29.5; 4/210

[56] References Cited

U.S. PATENT DOCUMENTS 3,161,891  12/1964  Bauman ................................... 4/110
3,750,647  8/1973  Gleason et al. ....................... 128/2 F Primary Examiner—Robert W. Michell
Assistant Examiner—Henry S. Layton
Attorney, Agent, or Firm—St. Onge, Steward, Johnston, Reens & Noe

[57] ABSTRACT

A device is described to enable the direct hygienic collection of a urine sample in a specimen tube. The collection aid is formed with a hollow body. A main opening of the hollow body is oriented to receive a female or male voiding stream which is confined in a chamber having specimen and excess urine outlet ports. The specimen outlet is shaped to releasably retain a specimen container such as a centrifuge tube while the excess urine outlet is effectively sized and selectively spaced from the specimen outlet to assure sufficient flow through the specimen outlet for a sample while enabling the remainder to be drained away. In one embodiment the hollow body is formed of relatively rotatable segments shaped to enable the hollow body to be adapted to be used for both male or females. Several embodiments are described.

9 Claims, 10 Drawing Figures

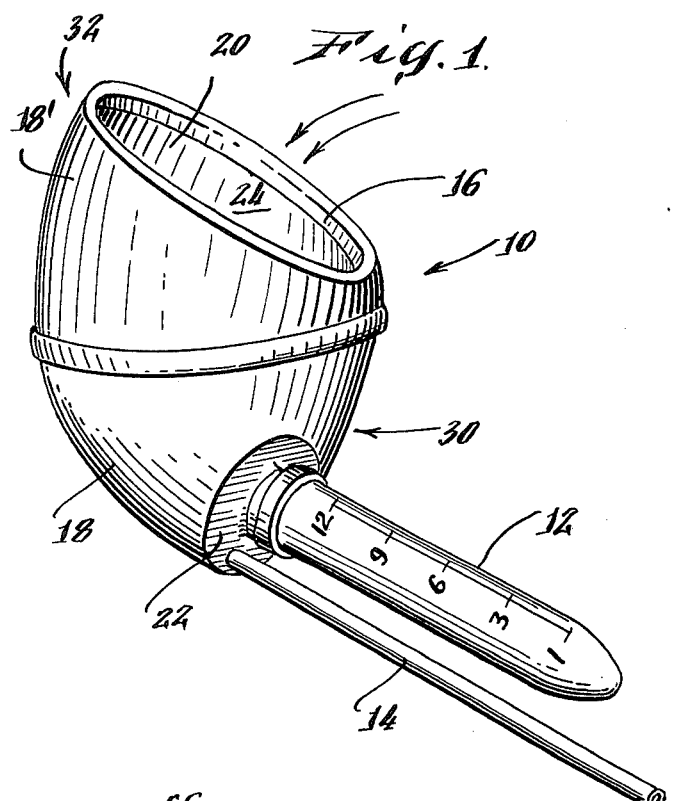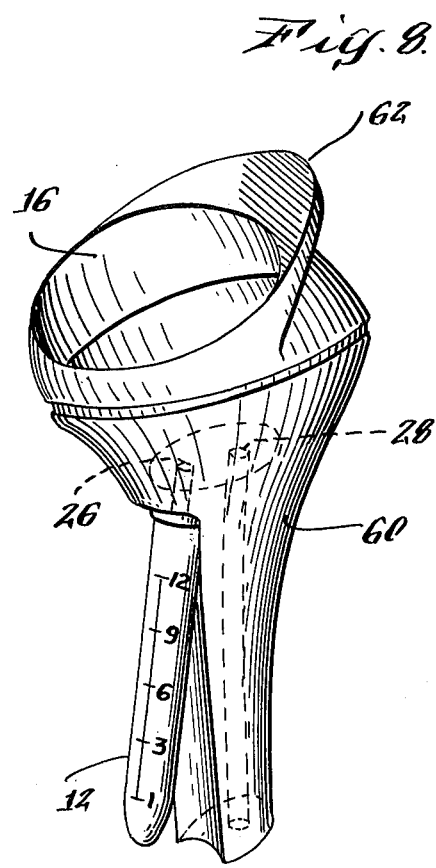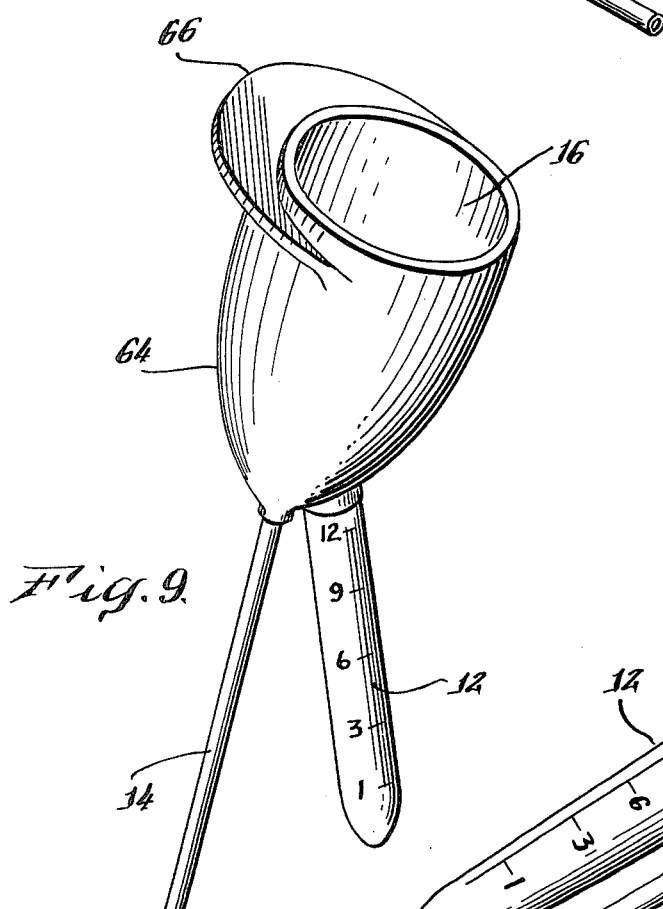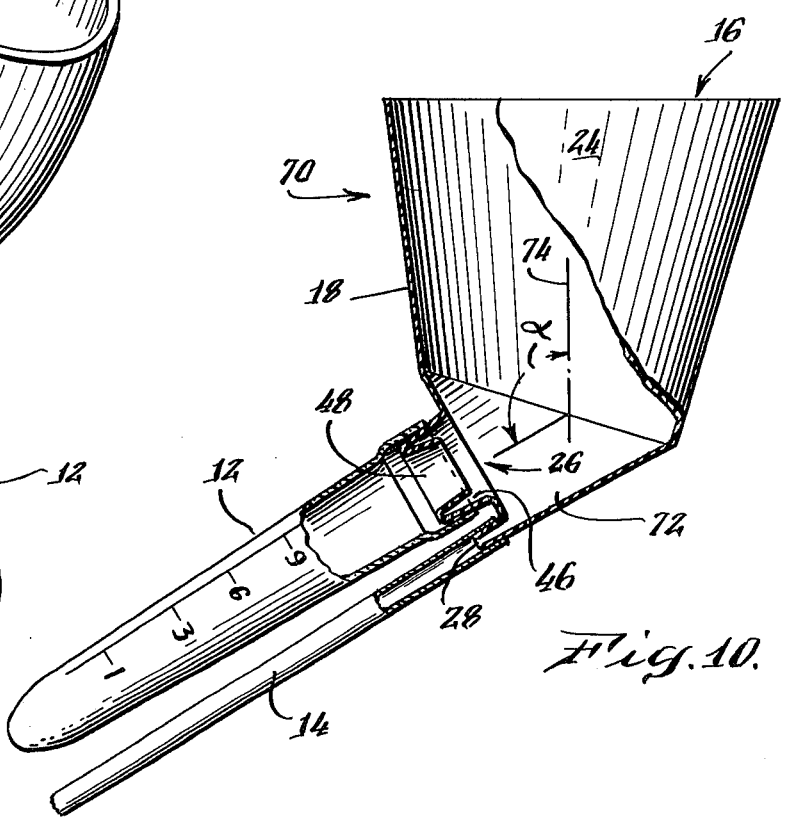

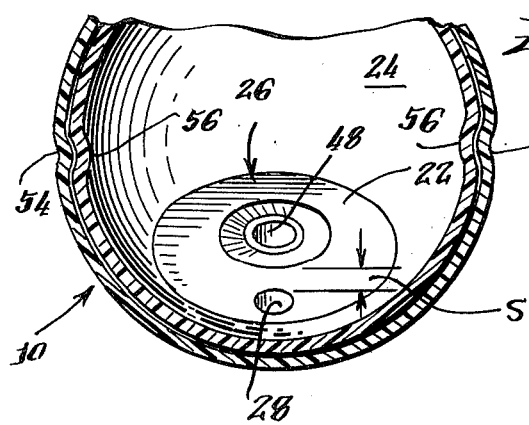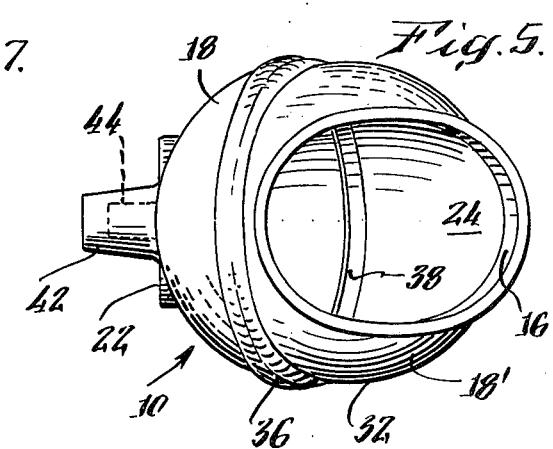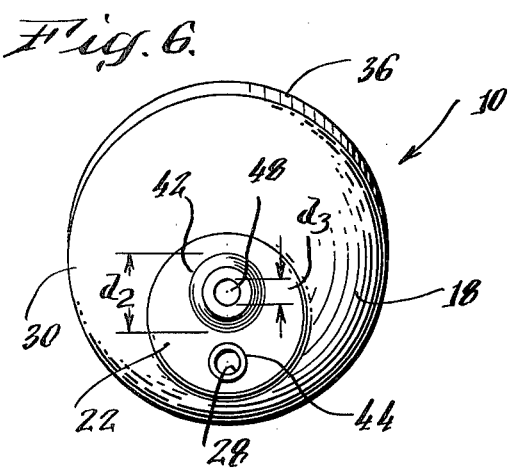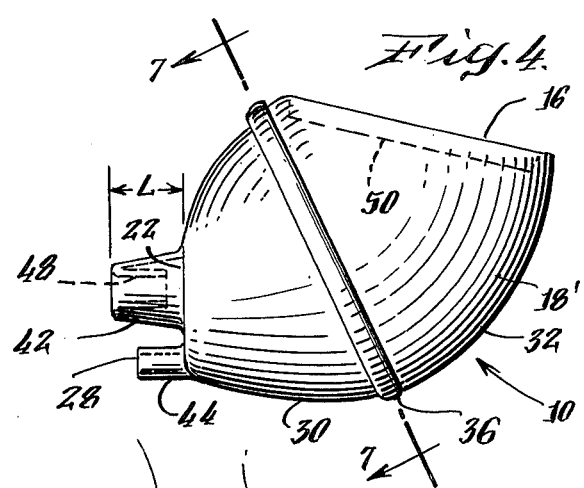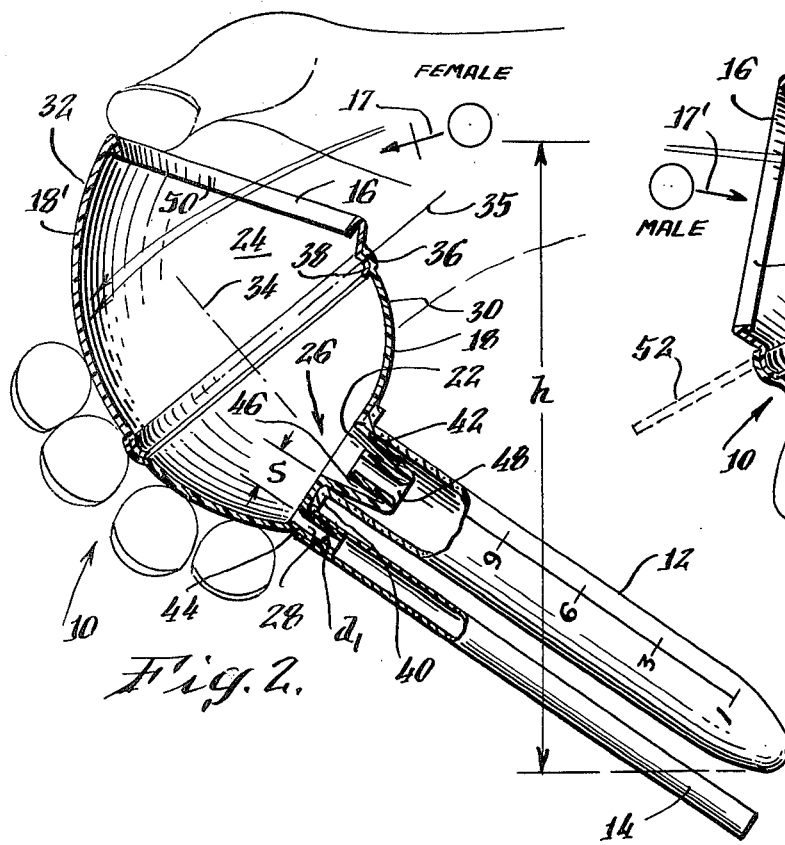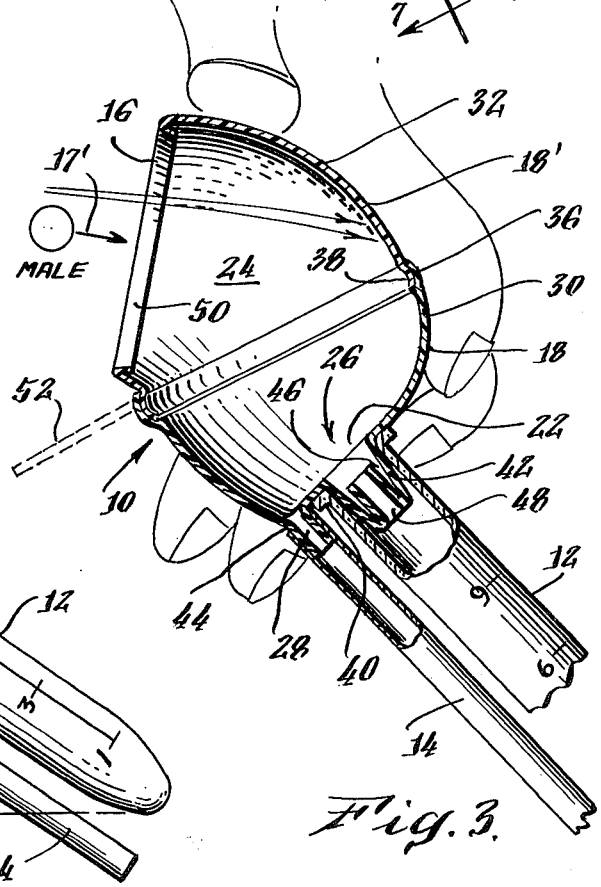

URINE COLLECTION AID

FIELD OF THE INVENTION

This invention relates to the field of urine collection systems. More specifically, this invention relates to a device for aiding in the collection of a urine sample in a specimen container.

BACKGROUND OF THE INVENTION

Systems or devices for aiding in the collection of urine specimen are widely employed. In the simplest and widely used form for a urine collection system a patient voids a sample in an open cup either directly or through a suitable funnel. The urine analysis sample is then taken from the cup and any remainder discarded with the cup. This approach often requires transfer to a more permanent container such as a centrifuge specimen tube for more convenient transport or for laboratory analysis. Manual handling of the filled cup may result in undesirable spillage, contamination of the urine specimen and can be of concern both to the nurse for having to handle a wetted cup or embarassment to the patient for being unable to present a clean sample.

In a more advanced urine collection system, a disposable specimen tube is employed in the urine collection process. Typically, such tubes have small openings and are limited in size to contain a sample, say from eight to twelve milliliters. These tubes are particularly adapted for direct use in centrifuge machines for urine analysis. In view of the small openings of such specimen tubes, it is still necessary for the patient to void first into a larger container such as a cup and then pour some of the cup contents into a specimen tube. The tube may then be capped, labeled and sent to a laboratory for analysis. The latter urine transfer often is accompanied by some spillage and particularly wetting of the tube outer surface.

The reliance upon a small, disposable collection cup introduces potential contamination problems for so-called "mid-stream" urine collection. It is generally recognized that the initial urine stream is likely to include bacterial and other contaminating components from the urinary tract. This is particularly so for females. Since such contaminants distort the analytical picture one can draw of the urine condition in the bladder, systems have been proposed to obtain urine specimen from the middle of the stream where the level of contaminants is substantially lower.

Available mid-stream collection devices take a wide variety of forms. For example, in one commercially available mid-stream collector, sterile cup and closures are provided. A person is instructed to interrupt voiding and then restart and take a sample which is voided in the cup. Though this procedure is acceptable for obtaining a mid-stream sample, it does not appear wholly free from contamination problems such as may occur from patient handling of the collection cup. As a result, current generally employed mid-stream collection procedures and devices represent a compromise in the purity of the sample. A device or technique which enhances the purity of the mid-stream sample by eliminating a potential source of contamination is highly desirable.

One technique for collecting a mid-stream urine sample from females is described in the U.S. Pat. to Gleason et al No. 3,750,647. As described, a mid-stream sample is taken by allowing the later and stronger voiding stream to enter a different exit port and container from that for the earlier and weaker voiding stream. Automatic mid-stream collection is claimed by use of such device.

The Gleason et al apparatus is specially shaped to adapt to the female urinary tract and relies upon the patient's control in positioning of the device to achieve the desired stream separation. As one well known in the art of urine collection devices can appreciate, the Gleason device is not likely to be free from contamination problems. The early voiding stream for example may impinge upon intermediate surfaces causing splashing. Such splashings from the early stream are likely to contaminate the mid-stream sample anyway. Furthermore, the Gleason device is particularly complex and does not appear to be conveniently usable for mid-stream collections from males.

Another urine specimen collector is described in the U.S. Pat. No. 3,635,091 to Linzer et al. This collector is designed specifically to automatically obtain a mid-stream specimen. The device includes an outer enclosure and a collapsible inner bag releasably connected to the main opening of the outer enclosure. The initial voiding stream is collected in the inner bag which pulls away from the main opening after a certain amount of urine has entered the bag. Therefore, the initial stream is trapped in the inner bag and a mid-stream sample is obtained from the outer enclosure. The collector on the whole, however, is bulky, complex and appears unlikely to avoid contamination of the specimen from the initial stream.

Other urine specimen collection devices can be found in the art such as the collapsible, disposable funnel structure described in U.S. Pat. No. 3,572,318 to T. N. Garland, or the double tube container in U.S. Pat. No. 3,859,671 to M. Pomasello. An overflow handle connected to a urine collection container is described in the U.S. Pat. No. 3,033,222 to F. X. Connolly. The U.S. Pat. to Beach, No. 3,923,040 discloses a specimen collector particularly adapted to fill a centrifuge tube.

SUMMARY OF THE INVENTION

In a urine specimen collection aid in accordance with the invention, a person, whether male or female, can freely void directly into a specimen tube without concern of overflow, or wetting problems. A specimen can be obtained in a hygienic manner with a disposable article which is shaped to receive and releasably retain a specimen tube at one end while accommodating a full voiding stream at a main opening.

As described with reference to one embodiment for a urine specimen collection aid in accordance with the invention, a hollow body is formed with a shape selected to reduce splashing of a voiding stream entering a main opening of the body. A wall extends downwardly from the main opening to form a urine flow confining chamber. The wall has a specimen outlet and an excess urine outlet with both outlets being located in urine draining positions at the bottom end of the wall. The outlets are further selectively spaced from each other so that the drain of urine through the excess urine outlet still permits the drain of urine through the specimen outlet when the hollow body is in an operative position.

A full voiding stream may enter the hollow body and enter a specimen tube while excess urine is drained away. A discharge conduit may be connected to the excess urine outlet so that urine can drain away without wetting of the specimen tube.

The excess urine and specimen outlets in the preferred embodiment are further so located that an incident voiding stream will tend to be initially drained by the excess urine outlet while later stream segments are favored to drain through the specimen tube. In this manner a mid-stream collection can be made without patient voiding interruption. Even when an interruption procedure is employed, the location of the specimen outlet permits the patient to release a full voiding midstream substantially without personal concern.

As described with reference to a preferred embodiment, a collection aid is formed of a pair of mating hollow segments which fit together with rotational motion about an exis selected to orient the main opening positions conveniently adapted for either male or female voiding.

With a urine collection aid in accordance with the invention, both male and female voiding can be accommodated with greater convenience, easier handling and in a hygienic manner. It is, therefore, an object of the invention to provide a urine collection aid which is useful to both male and female, can made at low cost to permit a hygienic one-time use, while providing a direct specimen tube sample without wetting.

These and other advantages and objects can be understood from the following description of several embodiments described in conjunction with the drawings.

DESCRIPTION OF DRAWINGS

FIG. 1 is a perspective view of a urine collection aid in accordance with the invention;

FIG. 2 is a section view of the urine collection aid when oriented for use in receiving a female voiding stream;

FIG. 3 is a section view of the urine collection aid when oriented for use in receiving a male voiding stream;

FIG. 4 is a side view in elevation of the urine collection aid of FIG. 1;

FIG. 5 is a top view of the urine collection aid of FIG. 4;

FIG. 6 is a front view in elevation of the urine collection aid of FIG. 4;

FIG. 7 is a section view of the urine collection aid taken along the plane defined by line 7—7 in FIG. 4;

FIG. 8 is a perspective view of an alternative form for a urine collection aid in accordance with the invention;

FIG. 9 is a perspective view of still another embodiment for a urine collection aid in accordance with the invention; and FIG. 10 is a section view of another embodiment for a urine collection aid.

DETAILED DESCRIPTION OF EMBODIMENTS

With reference to FIG. 1, a hollow body urine collection aid 10 is shown provided with a removable specimen centrifuge tube 12 and a removable excess urine discharge conduit 14 which may be in the form of a straw tube. The urine collection aid has a main opening 16 preferably sized to conveniently receive a voiding stream 17 from either a male or female person.

The urine collection aid 10 is formed with a wall 18 into a hollow body 10. The wall 18 extends from the main opening 16 to a bottom end 22 to define a urine flow confining chamber 24. The bottom end 22 is provided with a specimen outlet 26 and an excess urine outlet 28 (see FIGS. 2–7). The excess urine discharge conduit 14 extends generally alongside the specimen tube 12 and terminates past the end of tube 12 to a point selected to avoid wetting of tube 12 when in normal use.

In the embodiment of FIG. 1, the hollow body 10 is formed of a lower segment 30 and an upper segment 32. The lower segment includes the outlets 26, 28 and the upper segment has the main opening 16. The segments 30, 32 are matingly engaged for rotation about an axis 34, which is inclined relative to the plane of main opening 16. In this manner the urine collection aid 10 can be adapted for either male or female use by rotating the segments relative to each other.

Thus, with further reference to FIGS. 2–7 and initially to FIGS. 2 and 3, the urine collection aid 10 is shown with the upper segment 32 rotated in opposite positions about axis 34 which is perpendicular to a plane 35 of rotation. This plane is defined by annular mating ends 36, 38 of lower and upper segments 30, 32 respectively. Ends 36, 38 fit in rotational sliding relationship with each other by either a frictional engagement or a more positive snap fit as suggested in the illustrated embodiments with the slight outward curvature of ends 36, 38.

In the position of upper segment 32 in FIG. 2, the urine collection aid 10 is particularly adapted to receive a female voiding stream 17 whereby the overall vertical height, $h$, occupied by the aid while employed by a female is sufficiently small to conveniently accommodate a near-squatting position over a toilet bowl.

When the upper segment 32 is rotated 180 degrees from the position illustrated in FIG. 2, the urine collection aid 10 is conveniently employed to receive a male voiding stream 17' as shown in FIG. 3. Note that for both male and female uses, the excess urine drain 14 is below the specimen tube and thus, in addition to terminating past the bottom end of tube 12, further ensures convenient drainage without external wetting of the specimen tube 12.

One feature of the urine collection aid 10 in accordance with the invention is the shape of the urine confining chamber 24 for minimizing of splashing from voiding stream. In the selection of a shape, reference can be made to design suggestions published in a chapter "Design Considerations for Urination", pages 74–80 of a research report No. 7 entitled: *The Bathroom, Criteria for Design*, by Alexander Kira and published by Cornell University, Ithaca, New York in 1966 by its Center for Housing and Environmental Studies, Library of Congress Catalog No. 66–17889. In this report various toilet bowl designs are suggested with its FIG. 45 illustrating a preferred container having a continuously variable section to reduce splashing and noise.

Such design, however, is not directly applicable to a urine collection aid whose orientations are varied to accommodate the user and where splash minimization and convenience are major considerations.

Generally then, the shape of the urine flow-confining chamber 24 is formed with a wall 18 which extends downwardly and away from the main opening 16 at a generally non-splashing angle for both male and female uses. The orientation of the main opening 16 is selected so that a person will normally direct a voiding stream at the back side 18' of hollow body wall 18 as suggested by the voiding stream indicating arrows 17, 17'. In this manner the voiding streams are unlikely to impinge directly onto the bottom end 22 of the hollow body except perhaps with weak streams, in which case splashing is unlikely to be a problem anyway. The feature of enabling a simple rotation of upper segment 32 to accommodate both male and female voiding with minimum splashing strikingly enhances the hygiene of the urine sampling with the urine collection aid of this invention.

Another feature of the urine collection aid 10 involves the proximity of the excess urine outlet 28 to the specimen outlet 26 to influence the flow of urine through the latter outlet. The effective cross-sectional area A of the excess urine outlet 28 and its separation $s$ from the specimen outlet 26 are so selected that a sufficient amount of urine can flow into the specimen tube 12. These dimensions are selected further in view of the normally lower position of the excess urine outlet 28 when used by either a male or female person.

The cross-sectional area A of the excess urine drain outlet 28 generally should be sufficiently large to enable urine to drain away for particularly high flow rates without excessive back-up into the urine flow confining chamber 24. An excess back-up would create a head over the specimen outlet 26 and thus inhibit flow into the closed-ended specimen tube. On the other hand, if the outlet 28 is too large, all of the urine entering through main opening 16 will be directly drained away without allowing an adequate sample to enter the specimen tube 12 through outlet 26. The size of the excess urine outlet 28 should, therefore, be selected to enable a smooth flow of urine into the specimen tube. The draining capacity through the excess urine outlet 28 is selected by, for example, controlling the effective cross-sectional area with a constriction of the area of outlet 28 to assure a flow of urine into the specimen tube. When a possible peak urine flow of the order of about 30 ml per second is to be accommodated, the effective cross-sectional area A preferably is about 0.02 square inches or about one-quarter inch diameter for a circular outlet 28 and cylindrical discharge conduit 14.

This size can be increased, but one generally finds that small increases will be quickly noticed by a difficulty in filling of a specimen tube. Hence, the effective cross-sectional area of the drainage port 28 is selected somewhat smaller, particularly when the spacing $s$ between the outlets 26, 28 is increased or the entry level to the specimen outlet 26 is elevated above the outlet 28 instead of the flush bottom arrangement as shown in FIGS. 2-7.

The spacing $s$ between the excess urine outlet 28 and the specimen outlet 28 is selected in view of the normal vertically higher level of the specimen outlet 28 when in actual use. Thus a sufficient proximity must exist to enable urine to flow into the specimen outlet 26 as a result of a slight back-up at the excess drainage port 28. The spacing $s$ may be very small, but again not so little that it would become difficult to fit the wall 40 of the opening of tube 12 between the conduits 42 and 44 leading to outlets 26, 28 respectively.

The spacing $s$ further should not be so large as to require an excessive back-up of urine at the outlet 28. Generally, the separation for an embodiment as illustrated in FIGS. 2-7 preferably is in the range of about one-eighth to about three-eighths of an inch with a separation of about one-quarter of an inch preferred.

The hygienic advantage of a urine collection aid in accordance with the invention can be particularly appreciated with reference to the specimen outlet 26. This is in communication with specimen conduit 42 whose external dimensions are sized to extend into a specimen tube 12 while frictionally engaging the inside of its opening wall 40. The specimen conduit is provided with an effective cross-sectional area sized to displace a sufficient volume in a tube 12 so as to avoid its overflow when the tube 12 is withdrawn from the hollow body 18.

In the embodiment of FIGS. 2-7, the specimen conduit 42 has an annular return trap 46 is the form of an annular trough with a central through hole 48 leading into specimen tube 12. The size of the trap 46 is sufficient to displace enough volume in specimen tube 12 so that the urine level in the removed tube is below the top opening and not easily spilled. The tube 12 external surface thus remains dry when removed and can be conveniently capped without further spillage.

The external shape of conduit 42 is provided with a slight taper sufficient to frictionally engage and retain a specimen tube 12 during use while permitting tube removal such as by a simple twisting motion without urine spillage. The cross-sectional size of the urine catch 46 at the level of bottom 22 leading to hole 48 is sufficiently large to assure that a sufficient amount of urine will flow into the specimen tube 12. On the other hand, the catch area 46 should not be so large as to require either an excessive taper of conduit 42 to fit into a tube 12 or render the conduit 42 too long.

Generally a diameter, $d_2$, of from about seven-sixteenths to about nine-sixteenths of an inch for a circular catch is sufficient and permits an overall length L of the conduit 42 of about one-half inch. A diameter, $d_3$, of about five-sixteenths of an inch for the hole 48 is adequate.

In the sizing and location of the excess urine outlet port, another consideration is to limit the head of urine level over the specimen outlet port to a level selected to avoid urine overflow when the specimen tube is removed.

In the shaping and formation of the upper and lower segments 32, 30 several advantageous features are employed. Thus, the upper segment 32 is formed with a shape wherein the mating end 38 is circular and extends in a converging manner to a slightly elliptic main opening 16. The upper segment 32 is preferably shaped to as to permit its formation with a vacuum-molding process. The opening 16 includes an inwardly extending bend-over lip 50 to present a smooth edge facing a voiding stream.

The lower segment 30 is also preferably shaped in a manner whereby it can be vacuum molded. The upper end 36 is circular and converges from that end to a smaller circular bottom cross-section where the previously described outlet ports 26, 28 are located. The bottom 22 is shown as a flat surface; however, one may accommodate a gradually further converging shape whereby the wall of the lower segment 30 smoothly merges with the conduits 42, 44.

The vacuum molding process leaves a trim at end 36 and can be conveniently shaped to provide, for example, an edge (as suggested in phantom at 52 in FIG. 3), upon which edge 52 the urine collection aid 10 can rest while leaving the urine filled specimen tube 12 attached in an inclined position.

The two rotational positions of the upper segment 32 can be specifically identified by providing annular ends 36, 38 with suitable detents 54, 56 as shown in FIG. 7. The attachment of the segments 30, 32 can be completed right after molding or just prior to use. The advantage of later assembly resides in the ability to separately stack segments 30 and 32 with urine discharge conduits 14 and specimen tubes 12 for smaller bulk packaging.

The discharge conduit 14 can be a suitably shaped, preferably rigid tube such as a straw. The entire urine discharge flow rate is dependent upon its smallest cross-section. Hence, the desired smaller cross-section can be accommodated at the opening in bottom 22 or in the tube 14. For this reason, the referral herein to an effective excess urine outlet port includes such variations as may be found convenient to assure filling of the specimen tube 12 while avoiding excessive urine back-up into the urine flow confining chamber 24.

With reference to FIGS. 8 and 9, alternate embodiments for a urine collection aid are shown. In FIG. 8 a one-piece hollow body 60 is formed to which a specimen tube 12 can be releasably attached as described with reference to FIGS. 1-7. The hollow body includes a holding lip 62.

The collection aid shown in FIG. 9 includes a one-piece partial football-like shaped body 64 with a retainer lip 66. The specimen tube 12 and discharge conduit 14 can be as previously described.

In the embodiment of FIG. 10 a urine collection aid 70 is shown formed of a single molded structure but useful for male or female. The aid 70 has a converging wall 18 which extends from a generally circular opening 16 in a conically converging manner to a bottom part 72. The latter is further shaped into a funnel and inclined at an angle α relative to the axis 74 of the conical wall 18. The angle α is selected so that the specimen tube 12 may extend away from the aid when it is used. The overall length of the bottom part 72 is kept short so that a number of aids 70 can be conveniently stacked. The urine collection aid 70 is further preferably provided with outlet ports 26, 28 as previously described.

The aid 70 has a shape which enables a person to use it, though splashing is not likely to be as effectively inhibited as with the embodiments shown in the other Figures. An advantage of the aid 70 resides in its convenience for stacking and adaptability to low cost molding process.

Having thus described a urine collection aid in accordance with the invention, its advantage can be appreciated. A urine sample can be obtained in a hygienic manner, convenient for male or female persons. Variations from the described embodiments can be contemplated. For example, different types of specimen tubes 12 may be used and variations in the shape of the specimen conduit 42 can be made to accommodate these different tubes. The lower segment need not be oriented to a particular angle and be straight as shown in FIG. 9 as long as urine is guided to the outlet ports. The use of a separate or lower segment 30 permits use of a different material for enhanced frictional engagement with a tube 12 as well as between the upper and lower segments 30, 32. The embodiments described herein are for illustrating the inventive features and variations and departures therefrom may be contemplated within the scope of the claims.

What is claimed is:

1. An article for aiding in the direct collection of a urine sample in a specimen tube having an opening comprising
   a hollow body formed of a pair of relatively movable parts, one upper part having a main opening at an upper end of the hollow body as determined by its normal operative orientation, said main opening being sized to conveniently receive a urine voiding stream from either a female or male person, the other part being a lower part which matingly engages the upper part along a plane of rotation to enable the upper part to be rotated from a male position to a female position to effectively reduce the vertical height of the collection aid when employed to receive a female voiding stream, said hollow body being formed with a wall which extends downwardly from the main opening to form a urine flow confining chamber with the mating engagement of said upper and lower parts, said hollow body being further sized sufficiently small for manual retention and manipulation in proximity to the exit point of the voiding stream from a person;
   said wall further being provided at a bottom located lower segment of the lower part with specimen and excess urine outlets, said bottom located lower segment being selectively shaped to effectively guide the voiding stream to both of the outlets with normal operative orientation of the urine collection aid; and
   said specimen and excess urine outlets being selectively spaced relative to each other to enable excess urine to be drained away while a specimen sample of urine is passed through the specimen outlet for sample collection in a specimen tube having its opening in communication with the specimen outlet.

2. The urine collection aid as claimed in claim 1 wherein said upper and lower segments have circular ends sized to matingly engage each other with rotational motion.

3. The urine collection aid as claimed in claim 2 wherein said circular ends are curved to snap-fit to each other.

4. An article for aiding in the direct collection of a urine sample in a specimen tube having an opening comprising
   a hollow body having a main opening at an upper end of the hollow body as determined by its normal operative orientation, said main opening being sized to conveniently receive a urine voiding stream from either a female or male person, said hollow body being formed with a wall which extends downwardly from the main opening to form a urine flow confining chamber, said hollow body being further sized sufficiently small for manual retention and manipulation in proximity to the exit point of the voiding stream from a person;
   said wall further being provided at a bottom located lower segment of the urine flow confining chamber with specimen and excess outlets, said lower segment being selectively shaped to effectively guide the voiding stream to both of the outlets with normal operative orientation of the urine collection aid;
   said hollow body lower bottom located segment being provided with a conduit in communication with the specimen outlet, said conduit being sized to grippingly engage and protrude within the urine specimen tube and having an effective cross-sectional shape selected to provide sufficient urine displacement within the specimen tube to avoid urine overflow when a specimen tube is removed from the hollow body, said protruding conduit being provided with an internally located annular trough sized to retain said urine to avoid overflow; and said specimen and excess urine outlets being selectively spaced relative to each other to enable excess urine to be drained away while a specimen sample of urine is passed through the specimen outlet for sample collection in a specimen tube having its opening in communication with the specimen outlet.

5. The urine collection aid as claimed in claim 4 wherein the excess urine outlet has an effective cross-sectional area selected to limit urine drainage to a rate which is sufficiently slow to enable an adequate urine sample to flow through the specimen outlet.

6. The urine collection aid as claimed in claim 4 wherein the excess urine outlet is located at a bottom level which is selectively spaced with respect to the specimen outlet to limit the urine head over the specimen outlet to a level which enables said protruding conduit to guide urine through the specimen outlet while avoding urine overflow when a specimen tube is removed.

7. The urine collection aid as claimed in claim 6 wherein said excess urine outlet is provided with a urine discharge conduit shaped to frictionally engage said hollow body at the urine excess outlet, said discharge conduit having a sufficient length relative to that of the specimen tube to prevent wetting of a specimen tube when urine is drained through the discharge conduit.

8. An article for aiding in the direct collection of a urine sample in a specimen tube having a relative small opening comprising a hollow body having a main opening at an upper end of the hollow body as determined by its normal operative orientation, with the main opening sized to conveniently receive a voiding stream for a male or female person, said hollow body being formed with a wall which extends downwardly from the main opening to form a urine flow confining chamber;

said wall having a specimen outlet and an excess urine outlet, with both outlets being located in urine draining positions at the bottom end of the wall and selectively spaced relative to each other to enable the drain of urine through the excess urine outlet to influence the drain of urine through the specimen outlet with the hollow body in an operative position;

said hollow body being further formed of separate upper and lower segments, said lower segment having the specimen and excess urine outlets at the bottom end and terminating with the upper located circular end;

said upper segment having said main opening at an upper end and terminating with the lower located circular end; and both of said circular ends being sized to mesh with each other while permitting relative rotational motion between the upper and lower segments about an axis to position the main opening between male and female voiding stream receiving positions.

9. The urine collection aid as claimed in claim 8 wherein said main opening lies in a plane which is inclined relative to the axis of rotation between said segments to form an enlarged back wall for receiving female and male voiding streams.

* * * * *